United States Patent [19]

Gualandi

[11] 4,154,398
[45] May 15, 1979

[54] ROOM DEODORIZER DEVICE

[75] Inventor: Paolo Gualandi, Bologna, Italy

[73] Assignee: Polichimici Guaber S.p.A., Funo di Argelato, Italy

[21] Appl. No.: 855,787

[22] Filed: Nov. 28, 1977

[30] Foreign Application Priority Data

Dec. 9, 1976 [IT] Italy .............. 15225 B/76

[51] Int. Cl.² ............................................. A61L 9/04
[52] U.S. Cl. .................................................. 239/59
[58] Field of Search ............................ 239/58–60, 239/57

[56] References Cited

U.S. PATENT DOCUMENTS

| 2,131,975 | 10/1938 | Samstag | 239/59 X |
| 2,603,532 | 7/1952 | Wheeler et al. | 239/59 |
| 2,783,084 | 2/1957 | Paxton | 239/59 |
| 3,908,906 | 9/1975 | Crowle et al. | 239/58 |

Primary Examiner—Robert W. Saifer
Attorney, Agent, or Firm—Lowe, King, Price & Becker

[57] ABSTRACT

The deodorizer device consists of a top piece, shaped as an ashtray, and presenting on its lower side, below the ash-carrying bowl, a downwardly directed flange, into which flange there can be fitted a cup-shaped bottom piece inside which there is placed the deodorizer cake. Both the flange of the top piece and the side wall of the bottom piece present apertures that can be brought in or out of register, thus permitting or stopping the deodorizing activity of the gel cake which is at the interior of the cavity defined by the cup-shaped bottom piece fitted inside the flange of the ashtray-shaped top piece.

5 Claims, 5 Drawing Figures

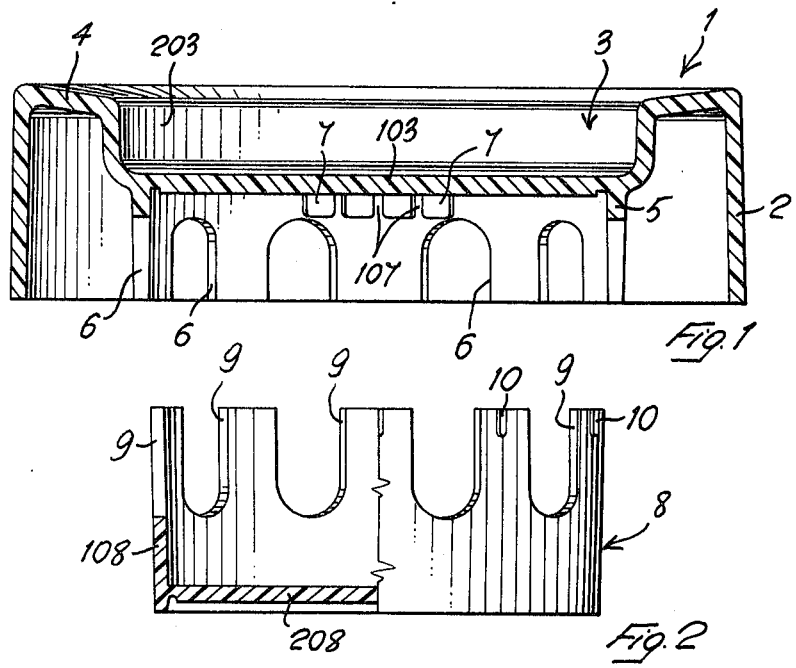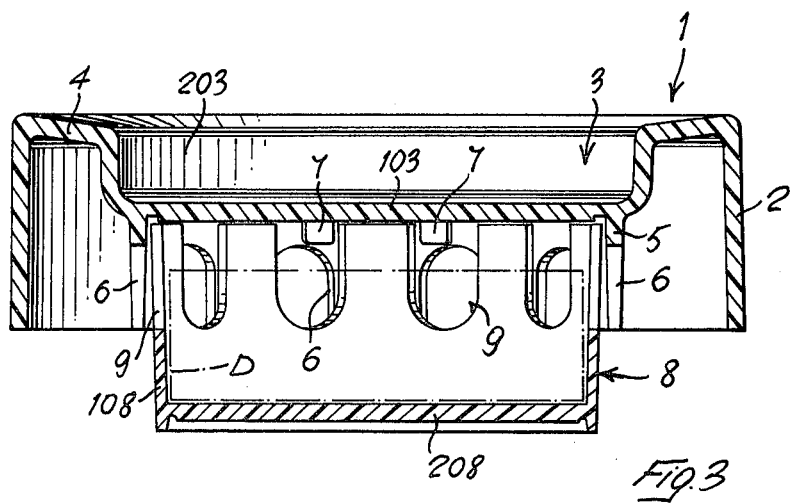

ROOM DEODORIZER DEVICE

SUMMARY OF THE INVENTION

This invention relates to room air treating devices, such as room deodorizers, and in particular to such deodorizer devices which obtain their effectiveness through evaporation of a solid volatile deodorizer substance, usually in the form of a gel cake.

According to the invention, the deodorizer device is characterized by the fact that it is constructed as an ashtray, presenting in its base or bottom section a cavity for housing the deodorizer cake, said cavity being provided with at least one aperture for permitting the aeration of the said cake, and thus the volatilization of the deodorizer substance.

More particularly, the deodorizer device consists of a top piece, shaped as an ashtray, and presenting on its lower side, below the ash-carrying bowl, a downwardly directed flange, into which flange there can be fitted a cup-shaped bottom piece inside which there is placed the deodorizer cake. Both the flange of the top piece and the side wall of the bottom piece present apertures that can be brought in or out of register, thus permitting or stopping the deodorizing activity of the gel cake which is at the interior of the cavity defined by the cup-shaped bottom piece fitted inside the flange of the ashtray-shaped top piece.

The deodorizer device according to the invention contemporarily meets the requirement of a deodorizing action the intensity and duration of which can be adjusted at will, and the requirement of an outer aesthetic appearance which consents to the said device to be compatible with the customary decor of a living room, bedroom, office room or other places where it is necessary.

Moreover, in consideration of the fact that the deodorizer device has also the function of an ashtray, there is to be noted that the deodorizing action is carried out on the same spot where it is particularly needed, i.e., in proximity of smokers. In view of this fact, the volatile substance of the deodorizer cake will be made particularly active against the cigarette smoke and the odors of the cigarette butts deposited in the ashtray.

The characteristic features of the invention, and the advantages deriving therefrom, will appear evident from the following detailed description of a preferred embodiment of same, made with reference to the attached sheets of drawings.

BRIEF DESCRIPTION OF THE DRAWINGS

FIG. 1 is a diametral section of the top piece or ashtray-shaped body for the deodorizer device according to the invention.

FIG. 2 is a diametral section, with parts in view, of the bottom piece or base cup, which can be rotatably coupled in a removable manner to the ashtray body of FIG. 1, so as to define together with this latter the cavity provided with adjustable openings, for containing the solid deodorizer substance.

FIG. 3 is a diametral section, which shows the components of FIGS. 1 and 2, coupled the one to the other in their normal use position.

DESCRIPTION OF THE PREFERRED EMBODIMENT

Figure 4:
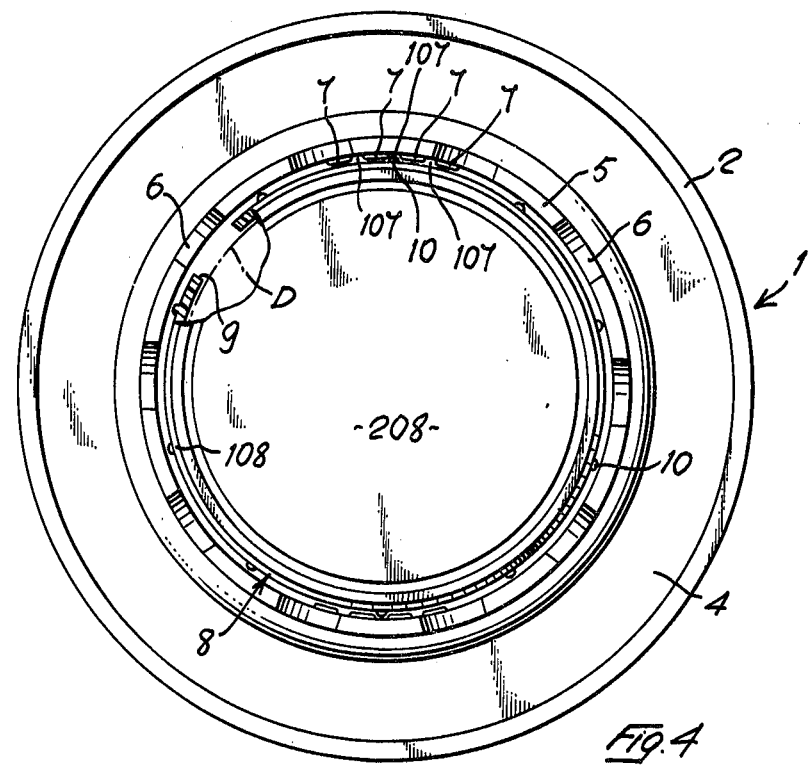
FIG. 4 is a plan view from the bottom, corresponding to FIG. 3, with a part of the base cup interrupted in order to evidence the position of complete register between the aeration opening of the base cup and of the inner flange of the ashtray body.

With reference to the Figures of the drawings, and firstly in particular to FIGS. 1 and 2 for the constructive particulars, reference numeral 1 indicates the top piece of the deodorizer device, which consists of an ashtray-shaped body, generally formed as a hollow circular body, having a relatively thin wall, with an outer skirt 2 directed downwardly substantially vertical or slightly inclined, and an ashtray bowl 3 defined by the bottom wall 103 and by the low sidewall 203, which is connected to the outer skirt 2 through the annular flanged portion 4, which is inclined towards the interior in the direction of the bowl 3.

In correspondence of the periphery of the bottom wall 103, the shaped body 1 presents on its underside an annular flange 5, which extends downwardly concentrically with respect to the skirt 2, and terminates substantially at the same level thereof. In said flange 5 there is formed a series of interspaced openings such as indentations or open slots 6 which, in the illustrated embodiment, define a crenelation with crenels opening downwardly. The flange 5 defines a head cavity which is open downwardly and is closed at the top by a ceiling constituted by the lower face of the bottom wall 103.

Figure 5:
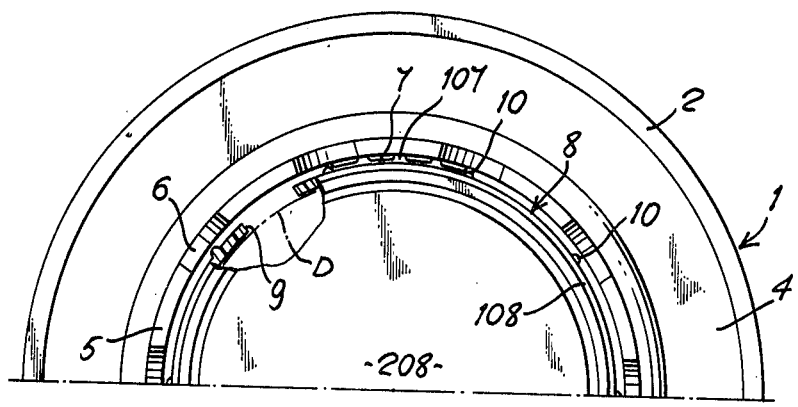
FIG. 5 is a partial plan view, similar to that of FIG. 4, with the aeration opening completely out of register.

Inside the above mentioned head cavity there is fitted the bottom piece of the deodorizer consisting of a base cup 8, provided with a crenelated side wall 108, presenting openings or slots 9 similar to the openings 6, angularly spaced between one another in equal manner, and also in equal number. In this manner, at a determined angular position of the cup 8 inside the flange 5, the openings 6 and 9 come to correspond with one another by pairs, in a position of perfect register. This is the case shown in FIGS. 3 and 4. Obviously, in another angular position, that is in another angular position of the top piece 1 of the deodorizer device with respect to the bottom piece 8, the openings 9 will result to be completely out of register with respect to the openings 6, until they result to be facing the closed spaces between said openings, as shown in the alternative position of FIG. 5. In this position the aeration of the deodorizer cake D arranged in the cavity of cup 8 is interdicted, so that no flow of deodorizer comes out of the apertures 6 and the cake is not consumed. Of course, there may be intermediate positions between the one of complete opening (FIG. 4) and the one of complete closure (FIG. 5), so as to regulate at will the intensity of the outflow of deodorizer. For this regulation, there may be provided indexing means at several intermediate positions. The said indexing means, as shown in the Figures of the drawings, may consist of interspaced projections 7 formed on the inner periphery of the circular flange 5, so as to define, between each two of them, suitable recesses or notches 107 apt to receive alternatively a bead or ridge projection 10 formed on the peripheral wall of the cup 8. The engagement of the ridge projection 10 in the said notches 107 defines in a stable manner the relative angular position between the ashtray piece 1 and the base cup 8.

The evaporation of the anti-smoke products, or other, may be easily regulated by controlling the rotation of the base cup with respect to the ashtray body, thus determining, in the various positions, the degree of register of the aeration openings, from which there depends the evaporation or volatilization intensity of the deodorizer substance which is active for predetermined purposes.

It is to be noted that the particular arrangement of the downwardly directed skirt 2 of the top piece of the deodorizer device has the precise function of concealing from sight the aeration openings 6, 9, thus efficaceously contributing to the aesthetic appearance of the ashtray.

It is believed that the invention will have been clearly understood from the foregoing detailed description of a preferred embodiment. Changes in the details of construction may be resorted to without departing from the scope of the invention as set forth in the appended claims.

I claim:
1. A room deodorizer device comprising:
   a top piece shaped as an ashtray and having on its underside a downwardly directed flange;
   a cup-shaped bottom piece having an upwardly directed side wall adapted to be fitted into said flange of said top piece to define a cavity therein for receiving a deodorizer substance;
   said flange including at least one opening therein adapted to be brought into registration with a corresponding opening in said side wall to permit aeration of the deodorizer substance; and
   a downwardly directed skirt at the periphery of said top piece spaced from said downwardly directed flange to conceal said openings from view.

2. A room deodorizer device according to claim 1, in which the flange of the top piece and the side wall of the bottom piece are both circular, and present an equal number of angularly equispaced openings.

3. A room deodorizer device according to claim 2, in which indexing means are provided in order to adjust and fix in position the top piece and the bottom piece according to various degrees of register of the respective openings.

4. A room deodorizer device according to claim 3, in which the indexing means are provided in correspondence of the confronting surfaces of the flange of the top piece and of the side wall of the bottom piece and consist of at least one bead-like projection on one surface, which engages notches or recesses provided on the other surface.

5. A room deodorizer device according to claim 1, in which the openings on the flange of the top piece and on the side wall of the bottom piece are formed as open slots or indentations.

* * * * *